(12) United States Patent
Corbeil et al.

(10) Patent No.: US 7,686,801 B2
(45) Date of Patent: Mar. 30, 2010

(54) METHOD AND APPARATUS FOR INDICATING PRESSURE IN CHEST DRAINAGE DEVICES

(75) Inventors: Scott E. Corbeil, Litchfield, NH (US); Nicholas Want, Manchester, NH (US); Theodore Karwoski, Hollis, NH (US); Scott Cadwallader, Northampton, MA (US); Adam Epstein, Wellesley, MA (US)

(73) Assignee: Atrium Medical Corporation, Hudson, NH (US)

( * ) Notice: Subject to any disclaimer, the term of this patent is extended or adjusted under 35 U.S.C. 154(b) by 1032 days.

(21) Appl. No.: 10/920,861

(22) Filed: Aug. 18, 2004

(65) Prior Publication Data

US 2005/0016287 A1  Jan. 27, 2005

Related U.S. Application Data

(63) Continuation-in-part of application No. 10/769,946, filed on Feb. 2, 2004, now Pat. No. 7,000,483.

(60) Provisional application No. 60/444,545, filed on Feb. 3, 2003, provisional application No. 60/468,728, filed on May 7, 2003.

(51) Int. Cl.
*A61M 27/00* (2006.01)
*A61M 1/00* (2006.01)
*G01L 7/20* (2006.01)
*G01L 7/00* (2006.01)

(52) U.S. Cl. ................... 604/541; 604/540; 73/748; 73/700

(58) Field of Classification Search ......... 604/317–331, 604/22, 540, 541, 184.04; 73/748, 700
See application file for complete search history.

(56) References Cited

U.S. PATENT DOCUMENTS

| | | | | |
|---|---|---|---|---|
| 4,063,556 A * | 12/1977 | Thomas et al. | ............... | 604/318 |
| 4,468,226 A * | 8/1984 | Kurtz et al. | ................. | 604/321 |
| 4,650,476 A * | 3/1987 | Telang | ........................ | 604/319 |
| 4,706,830 A * | 11/1987 | Wareing | ..................... | 215/365 |
| 4,715,855 A | 12/1987 | D'Antonio et al. | | |
| 4,747,843 A | 5/1988 | Felix et al. | | |
| 4,889,531 A | 12/1989 | D'Antonio et al. | | |
| 4,944,724 A * | 7/1990 | Goldberg et al. | ............ | 604/118 |
| 4,988,342 A | 1/1991 | Herweck et al. | | |
| 5,073,172 A * | 12/1991 | Fell | ............................. | 604/319 |
| 5,356,386 A * | 10/1994 | Goldberg et al. | ............ | 604/118 |
| 5,401,262 A | 3/1995 | Karwoski et al. | | |
| RE35,225 E | 4/1996 | Herweck et al. | | |
| 5,807,358 A | 9/1998 | Herweck et al. | | |
| 6,210,383 B1 | 4/2001 | Want et al. | | |
| 6,358,218 B1 | 3/2002 | Want et al. | | |
| 2003/0132249 A1* | 7/2003 | Romano | .................. | 222/181.1 |

* cited by examiner

*Primary Examiner*—Jacqueline F. Stephens
(74) *Attorney, Agent, or Firm*—RatnerPrestia (57) ABSTRACT

An apparatus is provided for indicating the presence of pressure within a collection chamber of a device such as a chest drainage device. The apparatus includes a bladder configured to be positioned within the collection chamber or within another chamber in fluid flow communication with the collection chamber. The bladder has a concavity formed therein and configured to contract or expand in response to pressure in the collection chamber. The apparatus also includes surfaces associated with the bladder that are configured to move with respect to one another upon contraction or expansion of the concavity of the bladder, thereby indicating pressure within the collection chamber.

9 Claims, 9 Drawing Sheets

METHOD AND APPARATUS FOR INDICATING PRESSURE IN CHEST DRAINAGE DEVICES

CROSS REFERENCE TO RELATED APPLICATIONS

This application is a continuation-in-part application of U.S. patent application Ser. No. 10/769,946, filed Feb. 2, 2004 now U.S. Pat. No. 7,000,483, which claims the priority benefit of U.S. Provisional Patent Application Nos. 60/444,545, filed Feb. 3, 2003, and 60/468,728, filed May 7, 2003. Each of the foregoing applications is incorporated by reference herein in its entirety.

FIELD OF THE INVENTION

This invention provides a method and apparatus for indicating pressure. More particularly, this invention provides methods and apparatus for indicating the presence of sub-atmospheric pressure in, or suction applied to, a chamber of a chest drainage device; a pressure differential between chambers of a chest drainage device; intra-pleural pressure; and/or for accessing the pleural cavity of a patient.

BACKGROUND OF THE INVENTION

Chest drains are often used in connection with cardiac and thoracic surgical procedures in order to remove fluids from the chest cavity of a patient. Suction is typically used to draw fluid into the chest drain. Various devices have been proposed for chest drainage over the years, including for example those disclosed in U.S. Pat. No. 4,988,342; U.S. Pat. No. Re. 35,225; U.S. Pat. Nos. 5,401,262; 5,807,358; 6,210,383; and 6,358,218, each of which is incorporated by reference herein.

Such devices may operate within a relatively small magnitude of suction and may include a suction regulator mechanism. For example, in some such devices, operation may occur in a range of −10 to −40 cm $H_2O$. Because they often apply suction directly to a patient's chest cavity, chest drainage devices ideally provide a low and consistent suction level that is compatible with human physiology.

Accordingly, it is desirable for chest drainage devices to include a suction monitor so that a medical professional can monitor the suction potential applied to the chest drainage device. For example, U.S. Pat. No. 5,807,358 discloses a passively-operated bellows in the form of a pleated polymer tube which has one end closed and another end opened and sealably affixed to an opening in a side wall of the chest drainage device. The outside of the bellows experiences the prevailing suction, and the bellows extends along a substantially horizontal line behind a face plate of the chest drainage device with its extension increasing as a greater degree of suction is applied. An elbow-shaped clear space can be provided in the face plate of the chest drainage device to improve the readability of the bellows.

It may also be desirable in chest drainage devices to monitor the level of suction that may be prevailing in the chamber in which fluids are collected from a patient's chest cavity. For example, as disclosed in U.S. Pat. No. 5,807,358, a float ball may be provided to ride up and down in a narrow column of water to indicate the level of excess suction prevailing in the collection chamber. If in the event that suction in the collection chamber exceeds the level of suction desired, the water level in the column rises and the position of the float ball thus warns the user of excessive negativity.

U.S. Pat. Nos. 4,715,855 and 4,889,531 disclose a fluid drainage system including a suction chamber and a fluid collection chamber. The system further includes diaphragm assemblies wherein flexing of a diaphragm operates a pressure measuring means. Specifically, a patient negativity diaphragm extends over an opening in a wall of a chamber, a push rod is attached to a diaphragm, and a dial is mounted on a pivot movable by the push rod for cooperating with a scale. When the atmospheric pressure outside of the chamber exceeds that in the chamber, the diaphragm flexes inwardly, rotating the dial to indicate the extent of patient negativity.

Also, the '855 and '531 patents disclose a gauge, provided to measure pressure in a suction chamber, that includes a diaphragm which covers an opening in a wall between an upper chamber (at atmospheric pressure) and the gauge (located in the suction chamber). The diaphragm flexes according to the pressure differential between the pressure in the chamber and atmospheric pressure, and such flexure is reflected in linear movement of a push rod, which in turn pivots a dial to reflect negative pressure on a scale.

U.S. Pat. No. 4,747,843 discloses a system pressure indicator connected to a chamber of a thoracic drainage device. The indicator provides, via sign means, a visual indication of whether the pressure in the collection container is negative or positive. A tubular elastomeric membrane is closed at its distal end and sealed by an O-ring at its proximal end. The sign means bears the letters "YES" to indicate negative pressure, and a magnifying lens is mounted in a cover panel so that the elastomeric membrane is visible through the lens. An aperture in the cover panel permits atmospheric air to enter the recess within which the indicator is positioned. When gases within the collection chamber are at negative pressure, the to elastomeric membrane collapses due to the higher atmospheric pressure on the outside of the membrane. In the collapsed state, the sign bearing the term "YES" is visible through the membrane, which indicates to the attending medical personnel that the collection container is under negative pressure. If the pressure in the collection container is positive, the membrane will expand and the word "YES" will not be visible, which indicates to the attending medical personnel that the pressure in the collection container is positive.

A visual indication of the level of applied suction is provided in the '843 patent by a transparent suction indicator flow tube and a flow ball. An aperture in the bottom of the flow tube allows atmospheric air to enter the bottom of the tube and the difference in pressure between the gas in a chamber and atmospheric pressure causes the ball to rise in the tube an amount proportional to the pressure difference, which may be indicated by a calibrated scale on the flow tube. The flow tube is positioned adjacent a front wall of the device for visualization.

Nevertheless, improvements to such chest drainage devices are continuously sought in order to improve performance, reduce cost, or improve the ease with which the devices are used by medical professionals.

SUMMARY OF THE INVENTION

According to one aspect of the invention, an apparatus is provided for indicating pressure within a collection chamber of a device such as a chest drainage device. The apparatus includes a bladder configured to be positioned within the collection chamber or within another chamber in fluid flow communication with the collection chamber. The bladder has a concavity formed therein and configured to contract or expand in response to pressure in the collection chamber. The apparatus also includes surfaces associated with the bladder that are configured to move with respect to one another upon contraction or expansion of the concavity of the bladder, thereby indicating pressure within the collection chamber. A corresponding method of configuring a device to indicate pressure within the collection chamber of the is device is also provided.

According to another aspect of this invention, an apparatus for indicating suction applied to a chamber of a device, such as a chest drainage device, is also provided. The apparatus includes a bladder, like that described above, but configured to be positioned within a chamber of the device that is coupled for fluid flow communication with a suction source. A corresponding method of configuring a device to indicate suction within a chamber of the device is also provided.

According to yet another aspect of the invention, an apparatus is provided for indicating a pressure differential between chambers of a device such as a chest drainage device. The apparatus includes a bladder, like that described above, but configured to be positioned within a chamber of the device, and configured to be coupled for fluid flow communication with another chamber of the device. An associated method of configuring a device to indicate a pressure differential between first and second chambers of the device is also provided.

According to still another aspect of this invention, an apparatus is provided for indicating intra-pleural pressure. The apparatus includes a chamber configured to be coupled for fluid flow communication with the pleural cavity of a patient and a bladder, like that described above, positioned within the chamber. A corresponding method of monitoring intra-pleural pressure is also provided.

Another aspect of this invention provides an apparatus for accessing the pleural cavity of a patient including a port configured to extend into the pleural is cavity of a patient; a chamber coupled to the port for fluid flow communication with the pleural cavity of the patient; and a bladder, like that described above, positioned within the chamber. Surfaces associated with the bladder move with respect to one another upon contraction or expansion of a concavity of the bladder, thereby indicating that the port is extending into the pleural cavity of the patient. A corresponding method for confirming proper placement of a device with respect to the pleural cavity of a patient is also provided.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

This invention will now be described with reference to several embodiments selected for illustration in the drawings. It will be appreciated that the scope and spirit of the invention are not limited to the illustrated embodiments. It will further be appreciated that the drawings are not rendered to any particular proportion or scale. Also, any dimensions referred to in the description of the illustrated embodiments are provided merely for the purpose of illustration. The invention is not limited to any particular dimensions, materials, or other details of the illustrated embodiments.

Referring generally to the exemplary embodiments selected for illustration in the Figures, an apparatus such as a sub-atmospheric pressure indicator 28 is provided for indicating the presence of sub-atmospheric pressure within a collection chamber 18 of a device such as a chest drainage device 10. The sub-atmospheric pressure indicator 28 includes a bladder 48 configured to be positioned within the collection chamber 18 or within another chamber in fluid flow communication with the collection chamber 18. The bladder 48 is configured to be coupled for fluid flow communication with atmosphere, and the bladder has a concavity 52 formed therein and configured to contract in response to sub-atmospheric pressure in the collection chamber 18. The sub-atmospheric pressure indicator 28 also includes surfaces 66 and 68 associated with the bladder 48 that are configured to move toward one another upon contraction of the concavity 52 of the bladder 48, thereby indicating sub-atmospheric pressure within the collection chamber 18.

An apparatus such as a suction indicator 30 is provided for indicating suction (the resulting suction) applied to a chamber of a device such as a chest drainage device 10. The suction indicator 30 includes a bladder 48, like that described above, but configured to be positioned within a chamber of the device that is coupled for fluid flow communication with a suction source (not shown).

An apparatus such as a pressure differential indicator 328 is provided for indicating a pressure differential between chambers 302 and 304 of a multi-chamber device 300 such as a chest drainage device. The pressure differential indicator 328 includes a bladder 348, like bladder 48 described above, but configured to be positioned within a chamber 302 of the device 300, and configured to be coupled for fluid flow communication with another chamber 304 of the device 300.

An apparatus such as pressure indicator assembly 100 is provided for indicating intra-pleural pressure. The pressure indicator assembly 100 includes a chamber configured to be coupled for fluid flow communication with the pleural cavity of a patient and a bladder 148, like bladder 48 described above, positioned within the chamber and coupled for fluid flow communication with atmosphere. A corresponding method of monitoring intra-pleural pressure is also provided.

An apparatus such as trocar device 200 for accessing the pleural cavity of a patient including a port such as trocar tip 205 configured to extend into the pleural cavity of a patient; a chamber coupled to the port for fluid flow communication with the pleural cavity of the patient; and a bladder 248, like bladder 48 described above, positioned within the chamber. Surfaces 266 and 268 associated with the bladder 248 move toward one another upon contraction of a concavity 252 of the bladder 248, thereby indicating that the port is extending into the pleural cavity of the patient. When a portion or surface of the indicator, such as edge portion 266, moves in response to contraction of concavity 252, that surface is visualized by the user of the device through indicating window 234.

Referring now to the specific embodiments selected for illustration in the Figures, FIGS. 1-6 show one exemplary embodiment of a chest drainage device 10 having a sub-atmospheric pressure indicator 28 and a suction indicator 30 according to aspects of this invention. Specifically, chest drainage device 10 is provided with a cover 12, which is shown in phantom in order to reveal internal details of the chest drainage device 10. The chest drainage device 10 includes an inlet 14 positioned to receive fluid from the pleural cavity of a patient. As will be understood, a tube or other conduit can be coupled to the inlet 14 for communication with the pleural cavity of a patient and to deliver fluid from the pleural cavity into the chest drainage device 10.

Figure 1:
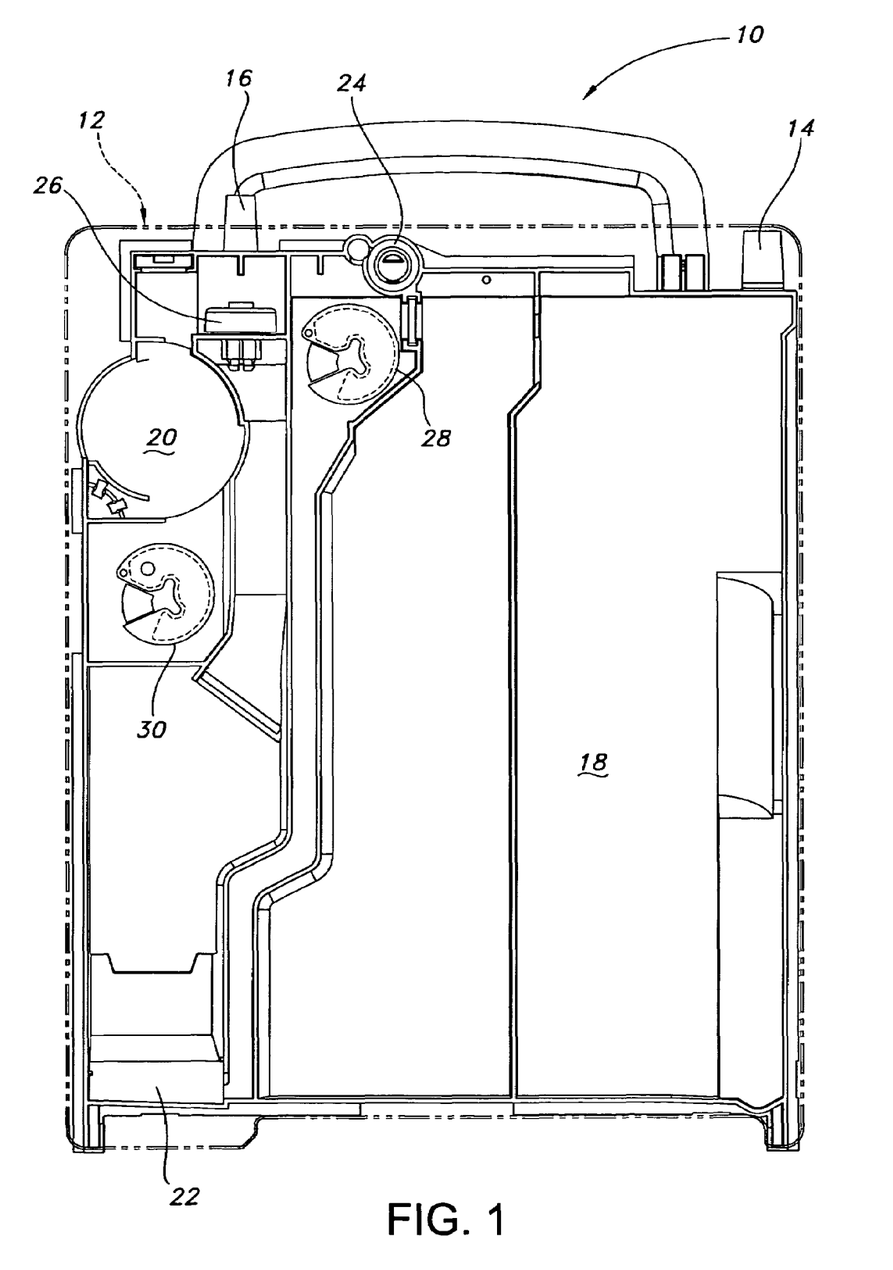
FIG. 1 is a front view of an exemplary embodiment of a chest drainage device according to aspects of this invention, with the cover of the chest drainage device shown in phantom in order to reveal internal details of the device.

The chest drainage device 10 also includes an outlet 16 positioned to be coupled to a source of suction. For example, a tube or other conduit can be is coupled to outlet 16 and to a suction source such as those typically found in a hospital or clinical setting. Accordingly, suction from a suction source is applied to the chest drainage device 10 via the outlet 16 in order to apply indirect suction to the pleural cavity of the patient via the inlet 14.

Chest drainage device 10 also includes a collection chamber 18 sized and positioned to receive and contain fluid from the pleural cavity of the patient, which fluid enters via inlet 14. In order to regulate the suction potential applied to the collection chamber 18, the chest drainage device 10 is provided with a suction regulator chamber 20 positioned to house a suction regulator such as the one disclosed, for example, in U.S. Pat. No. 5,807,358, incorporated herein by reference. The chest drainage device 10 is also provided with an air leak monitor 22, a high negativity manual vent valve 24, and a vacuum protection valve 26.

The sub-atmospheric pressure indicator 28 provides an indication of the presence of sub-atmospheric pressure within the collection chamber 18 of the chest drainage device 10. Details of the positioning, construction, and components of sub-atmospheric pressure indicator 28 are provided in FIGS. 2A, 2B, 3, 4A, 4B, 5A, 5B, and 6, and in the associated description below. Suction indicator 30 provides an indication of the suction applied to a chamber of the chest drainage device 10. The construction of the suction indicator 30 is similar to that of the sub-atmospheric pressure indicator 28, and will not be described separately.

Figure 2A:
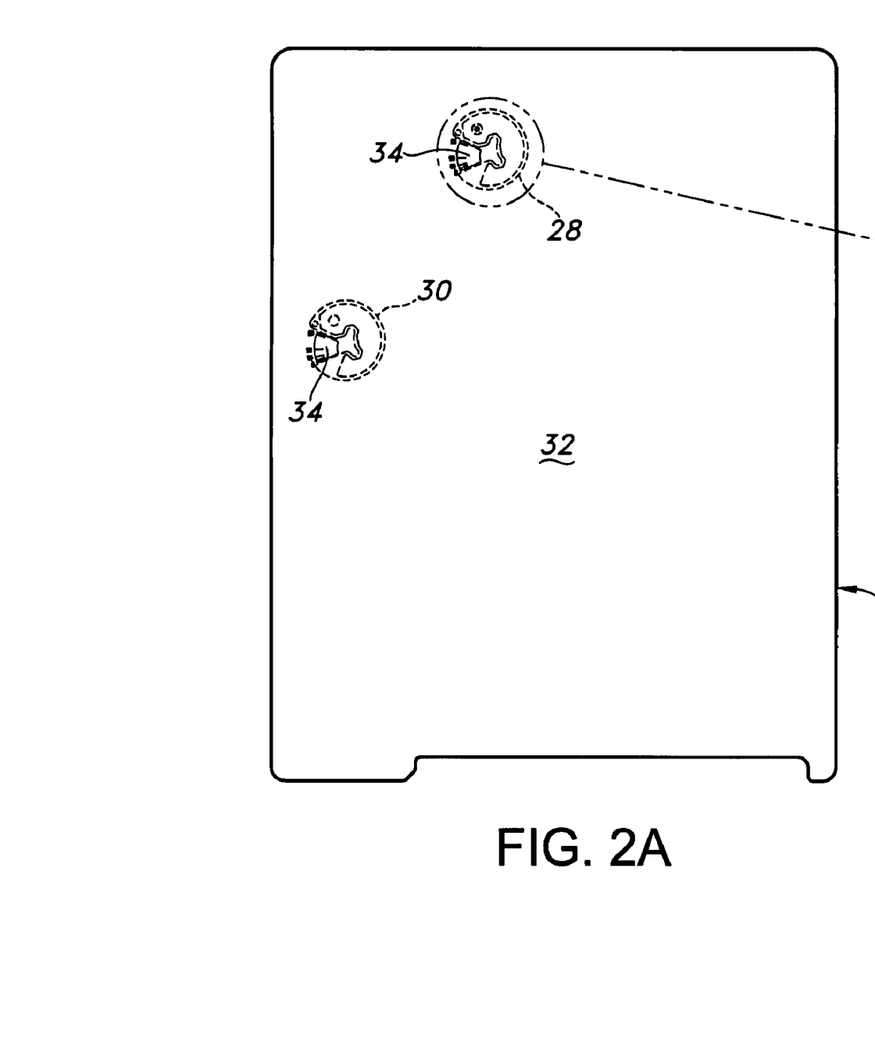
FIGS. 2A and 2B are front views of an exemplary embodiment of a cover component of the chest drainage device shown in FIG. 1.
Figure 2B:
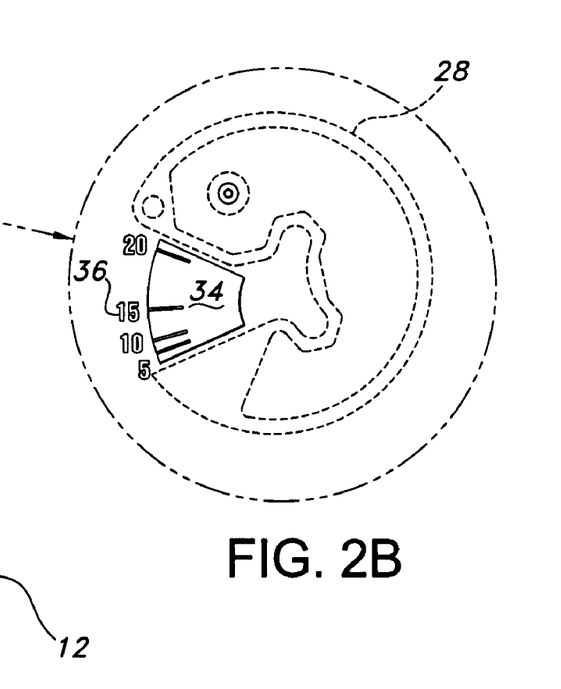

Referring now to FIGS. 2A and 2B, an exemplary embodiment of a cover 12 configured for use with the chest drainage device 10 is illustrated. FIG. 2A shows a front view of the cover 12, while FIG. 2B illustrates a detail of the cover 12 in the area of sub-atmospheric pressure indicator 28. Because the cover 12 includes a decoration 32, such as a decal, covering portions of its surface, the sub-atmospheric pressure indicator 28 and suction indicator 30 are shown in phantom.

The decoration 32 is provided with indicating windows 34, which permit a user of the chest drainage device 10 to see into the interior of the chest drainage device 10 during use. To facilitate such visualization, the cover 12 is optionally formed from a clear or translucent material, and the decoration 32 is optionally provided with a clear region to form each of the indicating windows 34. Associated with each of the indicating windows 34 is a pressure scale 36 indicating a range of sub-atmospheric pressures. For example, and for purposes of illustration, the indicating window 34 shown in FIGS. 2A and 2B are provided with a scale 36 having markers or indicia for $-5$, $-10$, $-15$, and $-20$ cm $H_2O$ of suction or negative pressure. Though negative signs are not shown on scale 36 in FIGS. 2A and 2B, such signs can be added or another indicia can be provided to indicate that the pressure is negative.

As will be described later in greater detail, at least a portion of the sub-atmospheric pressure indicator 28 and the suction indicator 30 illustrated in FIG. 2A will be visible to a user of the chest drainage device 10 through a respective indicating window 34, and the indicators 28 and 30 will indicate a value on a respective scale 36 when exposed to sub-atmospheric pressure or suction.

It will be understood that the scale 36 illustrated in FIG. 2B can include a wider or narrower range of sub-atmospheric pressures, and that the indicia on the scale 36 can be provided in fewer or greater increments. It is also contemplated that the numeric values provided on the scale 36, which provide a quantitative value of sub-atmospheric pressure, can be replaced by qualitative indicia or markings in order to provide limits or preferred operating ranges of sub-atmospheric pressure.

The scale 36 is alternatively applied to the surface of the indicator 28 for movement with respect to a surface of the device 10. For example, a scale can be embossed on the surface of the indicator 28 during a welding process, or graphics are optionally used to apply the scale to the indicator 28.

Figure 3:
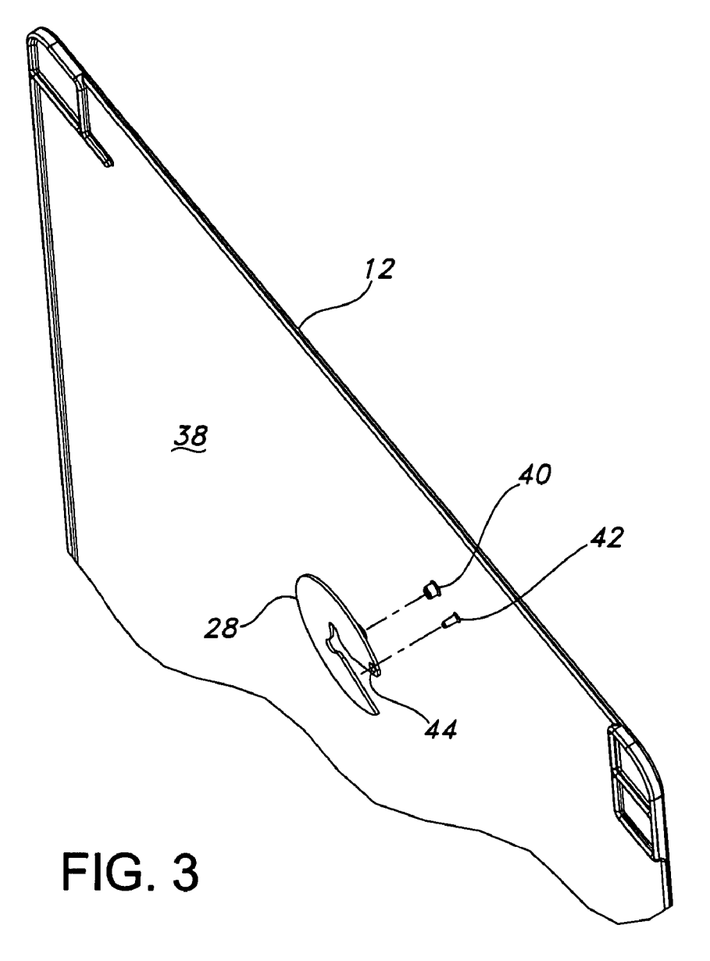
FIG. 3 is a perspective view of an exemplary embodiment of a sub-assembly of a pressure indicator and a cover of the chest drainage device shown in FIG. 1.

Referring now to FIG. 3, a sub-assembly of the chest drainage device 10 is illustrated to show the manner in which the sub-atmospheric pressure indicator 28 is coupled to the cover 12 of the device 10. Specifically, the cover 12 is provided with an inner surface 38, on which is formed an assembly boss 40 and an orientation alignment pin 42. The assembly boss 40, as will be described later in greater detail, provides an inlet port through which the interior (bladder) of the sub-atmospheric pressure indicator 28 communicates with the atmosphere external to the chest drainage device 10. The orientation alignment pin 42 meets with, and extends into, an orientation alignment hole 44 of the sub-atmospheric indicator 28 in order to maintain the alignment of at least a portion of the sub-atmospheric pressure indicator 28 with respect to the cover 12. More specifically, the orientation alignment pin 42, when mated with the orientation alignment hole 44 of the indicator 28, substantially prevents rotation of a portion of the sub-atmospheric pressure indicator 28 with respect to the cover 12 of the chest drainage device 10.

Although not shown in FIG. 3, suction indicator 30 is coupled to the cover 12 in the same manner as indicator 28. Accordingly, all descriptions of indicator 28 apply to indicator 30 as well.

Further details of the construction, mounting, and operation of the sub-atmospheric pressure indicator 28 will now be described with reference to FIGS. 4A, 4B, 5A, and 5B. While this description is made with reference to one exemplary embodiment of a pressure indicator (indicator 28), other pressure indicators that can be used in chest drainage device 10 are also described in pending U.S. patent application Ser. No. 10/769,946, filed Feb. 2, 2004, which claims the priority benefit of U.S. Provisional Patent Application Nos. 60/444,545, filed Feb. 3, 2003, and 60/468,728, filed May 7, 2003. Each of the foregoing applications is incorporated by reference herein in its entirety.

Figure 4A:
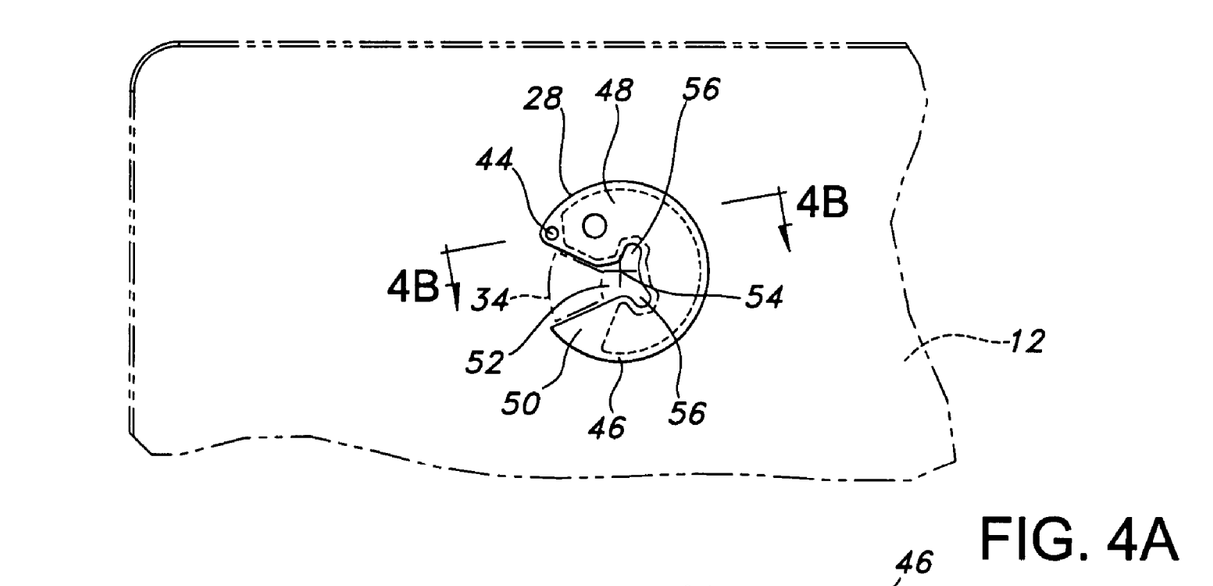
FIGS. 4A and 4B are front and cross-sectional side views, respectively, of the sub-assembly shown in FIG. 3, with the pressure indicator shown in a rest position without vacuum applied.

Referring to FIG. 4A, the sub-atmospheric pressure indicator 28 includes a seal 46 that forms a bladder 48. The seal 46 can be formed by a radio frequency (RF) welding process or any other known sealing process, including the use of molds, presses, ultrasonics, adhesives, and any other known means for forming a substantially sealed bladder. For example, using the RF welding process to form the seal 46 can be followed by a die cut operation.

The seal 46 is formed in such a way that a flag portion 50 is provided, which remains moveable with respect to the cover 12 of the chest drainage device 10. It is the flag portion 50 that can be visualized by a user of the device 10 through the indicating window 34 when sub-atmospheric pressure is applied to the collection chamber 18 of the chest drainage device 10.

The sub-atmospheric pressure indicator 28, and its associated bladder 48, is provided with a concavity 52, which (in the embodiment illustrated in FIG. 4A) extends inwardly into the bladder 48 beyond a center 54 of the sub-atmospheric pressure indicator 28. The concavity 52 is shaped in such a way as to facilitate the movement of the flag portion 50 of the indicator 28 when the pressure in the collection chamber 18 falls below the atmospheric pressure within the bladder 48, as will be described in greater detail with reference to FIGS. 5A and 5B. The concavity 52 includes recesses 56, thereby providing portions of the bladder 48 with a smaller width. These portions of bladder 48 therefore act as hinge regions or jointed portions in order to help facilitate the movement of the flag portion 50 and the contraction of the concavity 52. The extension of the concavity 52 beyond the center 54 of the indicator 28 also help facilitate the movement of the flag portion 50 and the contraction of the concavity 52.

Figure 4B:
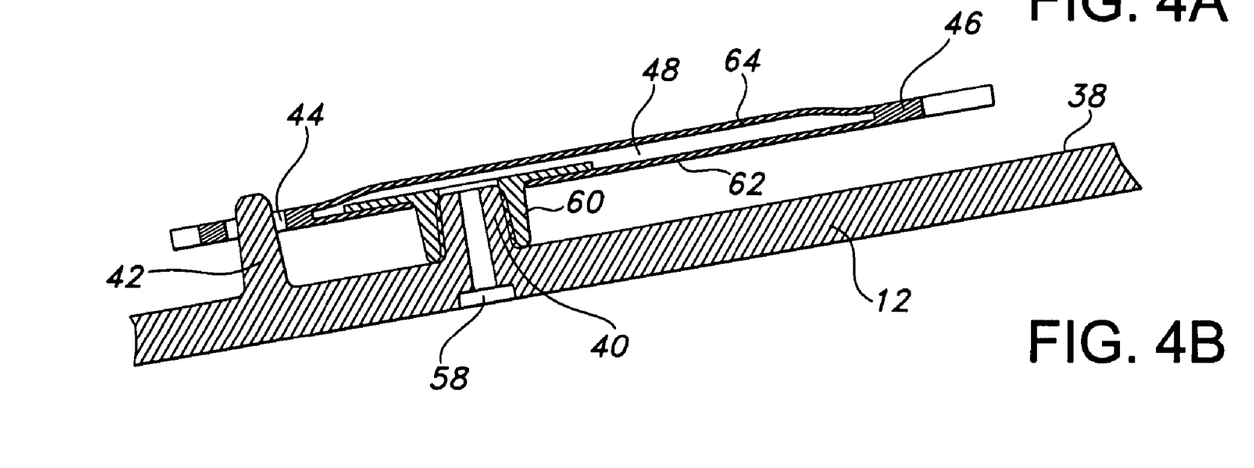

Referring to FIG. 4B, which provides a cross-sectional side view of the assembly of the cover 12 and the sub-atmospheric pressure indicator 28, the mounting of the indicator 28 to the back surface 38 of the cover 12 is illustrated. For example, FIG. 4B shows the relationship between the orientation alignment pin 42 extending from the inner surface 38 of the cover 12 and the orientation alignment hole 44 formed in the body of the sub-atmospheric pressure indicator 28. FIG. 4B also shows the relationship between the boss 40 formed on the inner surface 38 of the cover 12 and a "top hat" port component 60 of the indicator 28 (see FIG. 6 and associated discussion, below). An inlet port 58 is formed in the cover 12 and extends through the boss 40 in order to provide a passageway for fluid flow communication between the bladder 48 and the exterior of the chest drainage device 10 (atmosphere).

The sub-atmospheric pressure indicator 28 illustrated in FIG. 4B is formed from two film components 62, 64 that are sealed along seal 46 in order to define the bladder 48. While many film materials can be selected as a component of the indicator 28, a polyester film (such as a MYLAR film, for example) is optionally used. Film component 62 is thicker than film component 64 in this exemplary embodiment in order to control the inflated configuration of the bladder.

Figure 5A:
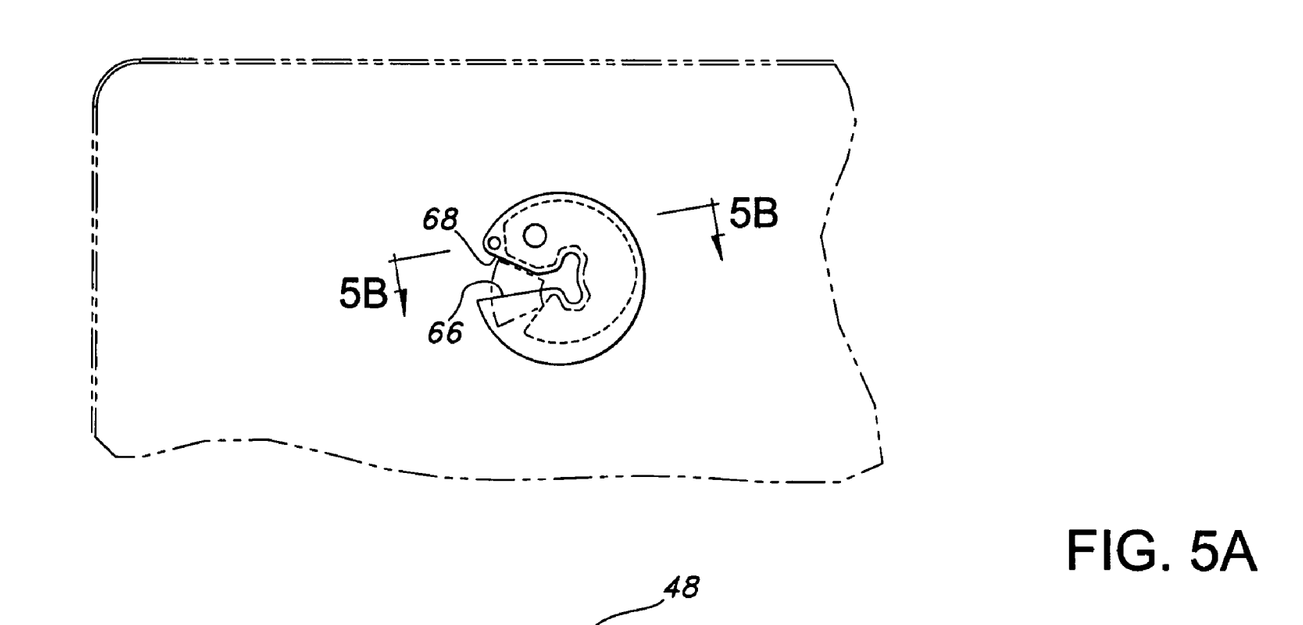
FIGS. 5A and 5B are front and cross-sectional side views, respectively, of the sub-assembly shown in FIG. 3, wherein the sub-assembly is shown with vacuum applied.
Figure 5B:
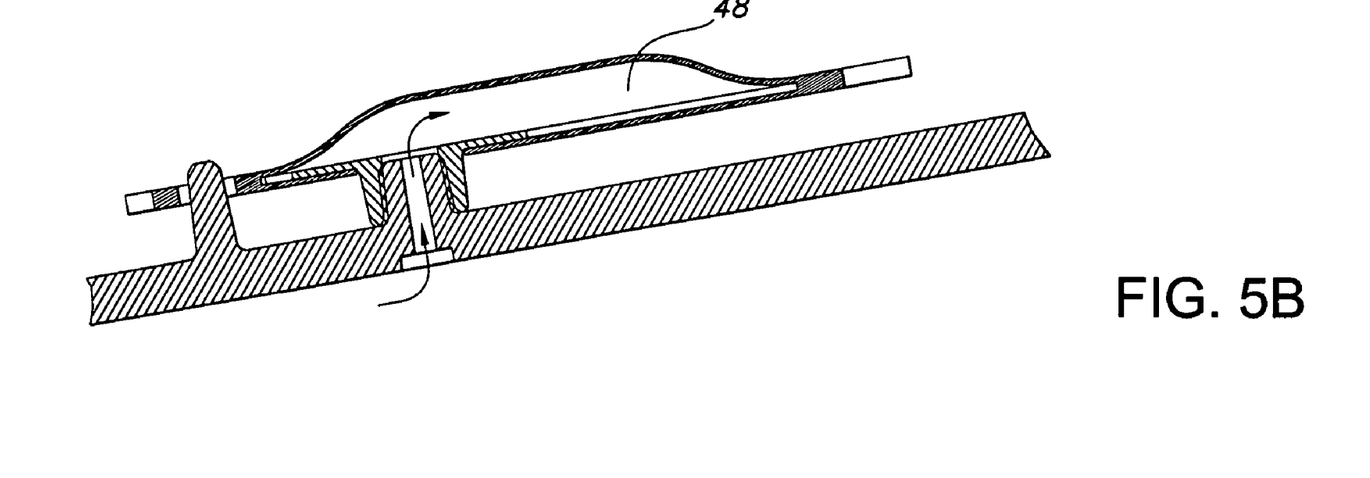

As shown in FIGS. 4B and 5B (described below), film component 62 optionally remains substantially planar in the inflated and deflated conditions, at least compared to film component 64. For example, film component 62 can be formed from a film having a thickness of about 2.5 MIL, and the film component 64 can be formed from a film having a thickness of about 0.9 MIL. Accordingly, the ratio of the thickness of the film component 62 to that of the film component 64 in the illustrated embodiment is about 2.5:1 or greater, though other ratios, including a 1:1 ratio, are contemplated as well.

Alternatively, film component 62 optionally balloons outwardly in the inflated condition like film component 64. Whether, and how much, film component 62 and/or film component 64 changes shape upon inflation or deflation depends on design choice.

A portion of the film component 62 and/or the film component 64 is optionally inked to assist visualization by the user. Alternatively, pigmented film can be used or other indicia can be applied to the indicator 28 or surfaces of the indicator 28 such as selected edge portions.

Referring now to FIGS. 5A and 5B, the sub-atmospheric pressure indicator 28 is provided with a pair of surfaces such as edge portions 66 and 68. Edge portion 66 is an outer boundary of the flag portion 50 and provides an indicia for alignment with the optional scale in the indicating window 34. More specifically, it is the edge portion 66 that can be visualized by a user of the chest drainage device 10 when sub-atmospheric pressure is applied to the collection chamber 18 and the bladder 48 expands in such a way as to move the flag portion 50 with respect to the surface of the cover 12.

While edge portions 66 and 68 are optionally selected to provide one or more surfaces for visualization by a user of the indicator 28, it is contemplated that any surface or surfaces associated with or coupled to the bladder 48 are optionally selected. For example, any surface of the bladder 48 can be used, whether that surface is at or adjacent any edge portion of the bladder 48 or is spaced from an edge portion of the bladder 48. Also, a surface of a component extending from or coupled to the indicator 28 or bladder 48 is optionally selected for visualization.

As the bladder 48 expands (as shown in FIG. 5B), the configuration of the pressure indicator 28 (by virtue of the concavity 52 and the recesses 56) changes in such a way that the edge portion 66 moves toward the edge portion 68. Edge portion 68 remains substantially stationary with respect to the cover 12 by virtue of the engagement between the orientation alignment pin 42 and the orientation alignment hole 44. In other words, as the bladder 48 expands and the configuration of the indicator 28 changes, the edge portion 68 remains in substantially the same position while edge portion 66 moves closer to edge portion 68. In such motion, the concavity 52 contracts.

Alternatively, bladder 48 can be configured such that surfaces associated with the bladder move with respect to one another in any direction. For example, such surfaces need not move toward one another. They can instead move away from one another or laterally with respect to one another. Such relative movement may depend on the shape and configuration of the bladder, including the positioning of any concavity formed in the bladder, or may depend on the relative pressures inside and outside the bladder, the surfaces selected for movement with respect to one another, and other factors.

The appearance of the expanded bladder 48 is illustrated in FIG. 5B. The arrows indicate the path of atmospheric air from outside the body of the device 10, through the inlet 58, and into the interior region of the bladder 48.

Though various configurations are contemplated, an angle between surfaces 66 and 68 may be predetermined based on a selected range of movement of the surfaces with respect to one another. For example, the angle formed between surfaces 66 and 68 and the configuration of the bladder 48 may be selected to provide a range of movement over a predetermined pressure range. In one exemplary embodiment, the free edge portion 66 may move about 45 degrees or more through a range of pressures from about 0 to −20 cm $H_2O$.

Figure 6:
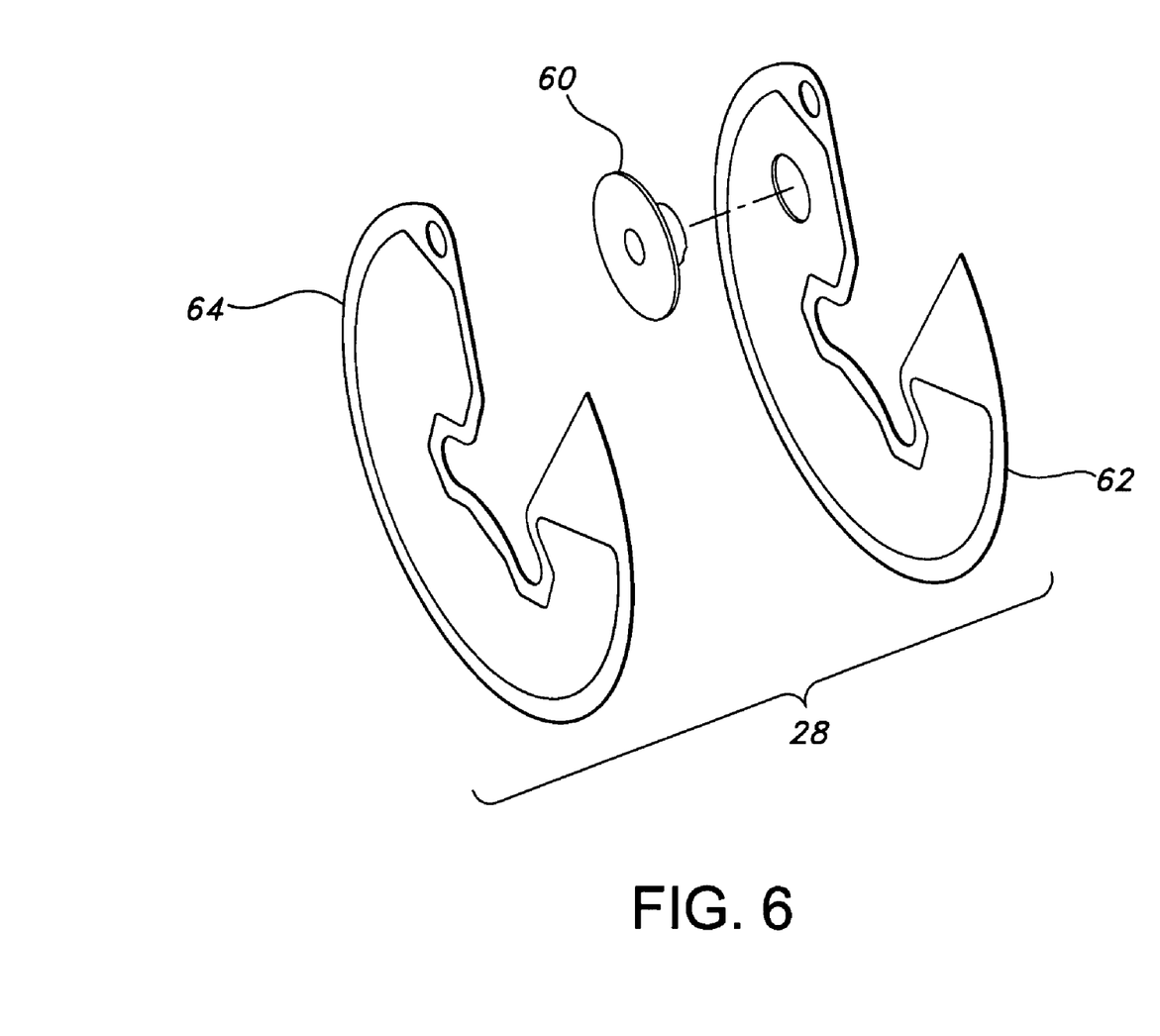
FIG. 6 is a perspective, exploded view of an exemplary embodiment of a pressure indicator according to an aspect of this invention.

Turning to FIG. 6, an exploded view of the components of the sub-atmospheric pressure indicator 28 is provided. As mentioned previously, the pressure indicator 28 is formed from an assembly of a "top hat" port 60 sandwiched between two opposed films 62 and 64. The top hat 60 provides both a port for the passage of atmospheric air into the bladder 48 (via inlet 58) and a structure for securely mounting the pressure indicator 28 to the back surface 38 of the cover 12 (on the assembly boss 40). Except for the engagement between the orientation alignment pin 42 and the orientation alignment hole 44, and except for the coupling of the top hat 60 to the assembly boss 40, the pressure indicator 28 is substantially unsupported by the cover 12, thereby permitting the change in the configuration of the pressure indicator 28 upon exposure to sub-atmospheric pressure.

Figure 7:
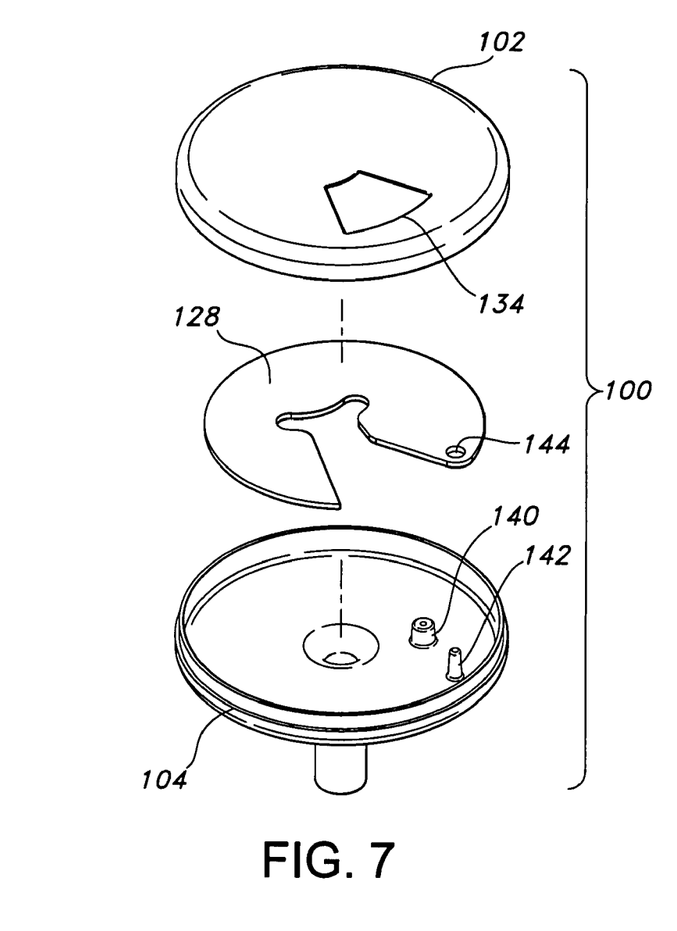
FIG. 7 is a perspective, exploded view of an exemplary embodiment of a pressure indicator assembly according to another aspect of this invention.
Figure 8:
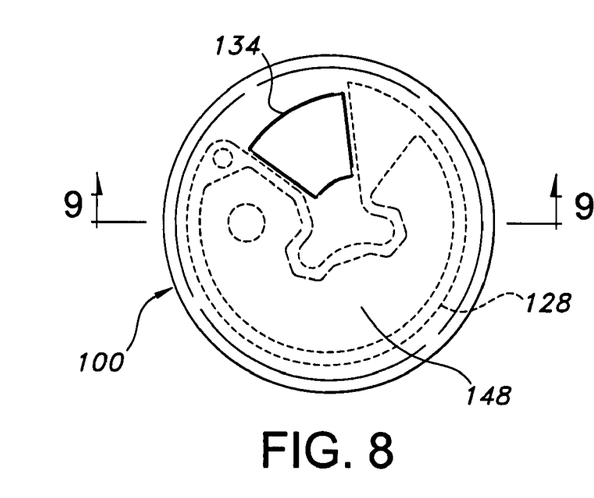
FIG. 8 is a top view of the pressure indicator assembly shown in FIG. 7.
Figure 9:
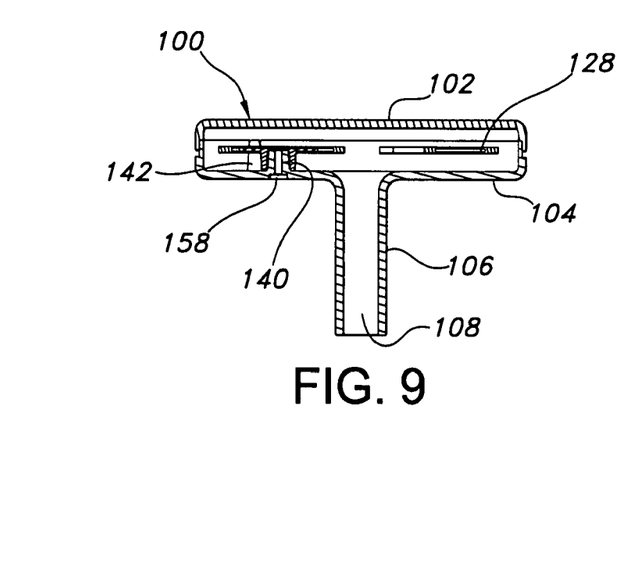
FIG. 9 is a cross-sectional side view of the pressure indicator assembly shown in FIGS. 7 and 8.
Figure 10:
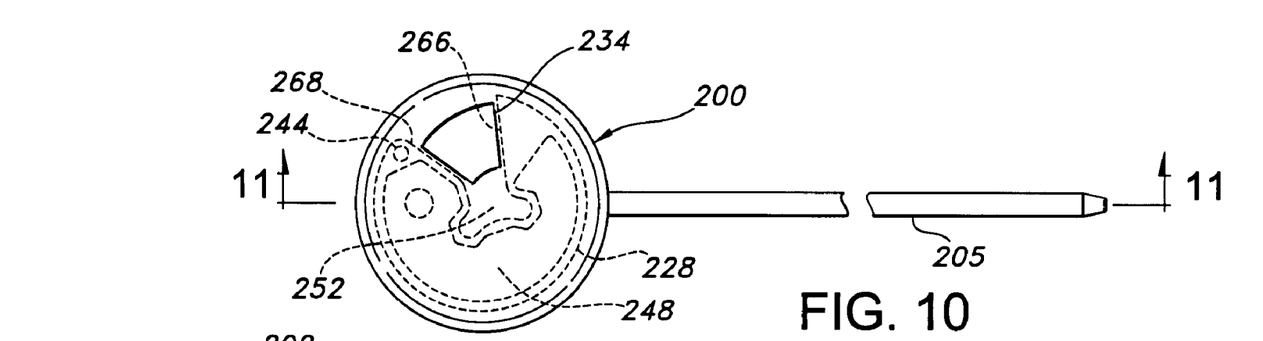
FIG. 10 is a top view of an exemplary embodiment of a device according to yet another aspect of this invention.
Figure 11:
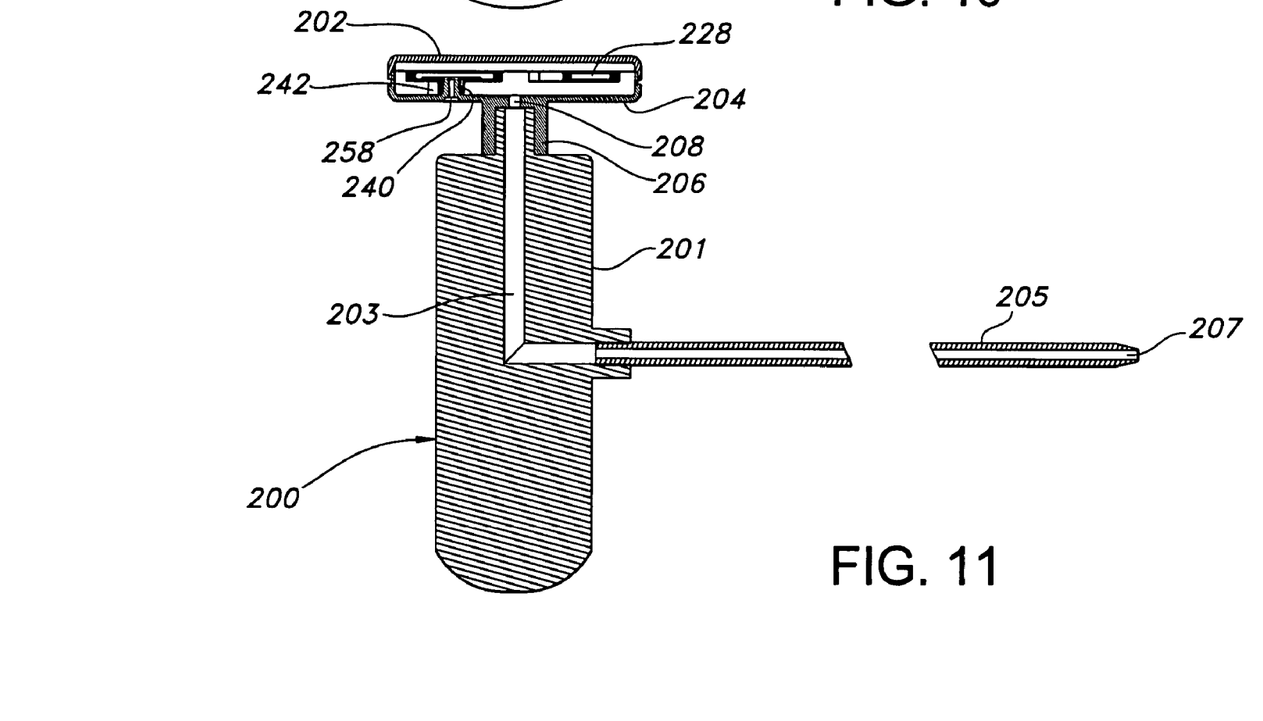
FIG. 11 is a cross-sectional side view of the device shown in FIG. 10.
Figure 12:
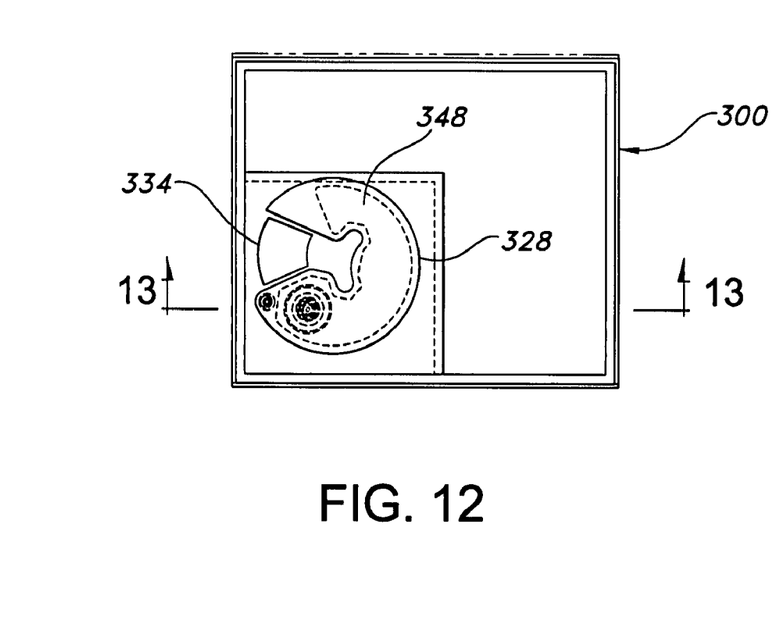
FIG. 12 is a top view of an exemplary embodiment of a multi-chamber system including a pressure differential indicator according to still another aspect of this invention.
Figure 13:
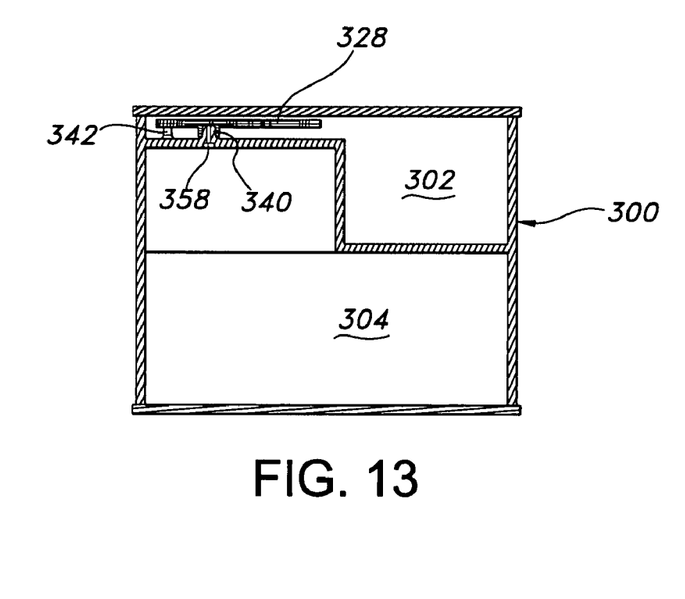
FIG. 13 is a cross-sectional side view of the multi-chamber system shown in FIG. 12.

FIGS. 7-13 illustrate exemplary embodiments of devices according to other aspects of this invention, each of which includes a pressure indicator similar to sub-atmospheric pressure indicator 28. Specifically, FIGS. 7-9 illustrate an embodiment of a pressure indicator assembly 100 that can be coupled for communication with the pleural cavity of a patient (or another pressure-containing chamber), FIGS. 10 and 11 illustrate an exemplary embodiment of a trocar device 200 configured for access to the pleural cavity of a patient, and FIGS. 12 and 13 illustrate a schematic representation of a multi-chamber system 300 in which a pressure indicator can be used to determine the pressure differential between chambers of the system.

Referring specifically to FIGS. 7-9, the pressure indicator assembly 100 includes a cap 102 and a body 104, which together form a chamber in which a pressure indicator 128 is housed. The body 104 of the pressure indicator assembly 100 includes an end adaptor 106 that is configured for connection to another component (e.g., a luer connection). An adaptor 106 of the body 104 defines a fluid flow passageway 108 for the communication of fluid flow between the chamber defined by cap 102 and body 104 and another pressure-containing body such the pleural cavity of a patient.

The pressure indicator assembly 100 includes a sealed indicating window 134 formed in the cap 102 to permit a user to visualize the pressure indicator 128 mounted within the chamber of the pressure indicator assembly 100. Indicating window 134 is similar to indicating windows 34 of the chest drainage device 10, and the pressure indicator 128 is similar in construction to the sub-atmospheric pressure indicator 28 of chest drainage device 10. The cap 102 is optionally clear or translucent and is optionally covered with a decoration 32, such as a decal, and may be provided with a window.

The mounting of the pressure indicator 128 is also similar to that in chest drainage device 10. Specifically, a "top hat" component of the pressure indicator 128 is mounted on a boss 140 of the body 104 of the pressure indicator assembly 100, and an inlet 158 provides for the flow of atmospheric air into the bladder 148 of the pressure indicator 128. Also, an orientation alignment pin 142 extending from the body 104 of the pressure indicator assembly 100 extends into an alignment hole 144 of the pressure indicator 128, thereby restricting movement of a portion of the pressure indicator 128 with respect to the body 104 of the assembly 100.

It will be appreciated that the pressure indicator assembly 100 can be used to indicate, measure, or sense sub-atmospheric pressure in a pressure-containing chamber by means of a connection of the end adaptor 106 of the pressure indicator assembly 100 directly or indirectly to a pressure-containing chamber. In other words, the chamber defined by the cap 102 and body 104 of the pressure indicator assembly 100 can be placed in fluid flow communication with any other body in order to detect or measure sub-atmospheric pressure in that other body. The manner of connection between the body 104 and another device or conduit can take a wide variety of forms including, for example, a luer connection, a barbed connection, a direct connection, or any other known means for defining a fluid flow passageway between the chamber of the pressure indicator assembly 100 and the atmosphere that is being monitored. Also, the pressure indicator assembly 100 can be used in conjunction with a catheter, an introducer, a trocar (as described below), a stylet, or any other such medical device or instrument.

The pressure indicator assembly 100, or the pressure indicator 128 used therein, can be mounted along any fluid path connected to the pleural space. For example, the pressure indicator assembly 100 can be coupled for fluid communication to any such path at any location.

Referring now to FIGS. 10 and 11, a trocar device 200 utilizes a pressure indicator 228 similar to the sub-atmospheric pressure indicator 28 in order to confirm that the trocar device 200 is properly positioned with respect to the pleural cavity of a patient. Specifically, like the pressure indicator assembly 100 illustrated in FIGS. 8 and 9, the trocar device 200 includes a cap 202 and a body 204 defining a chamber in which the pressure indicator 228 is mounted. The body 204 includes an end adaptor 206 in order to couple the body 204 to a body 201 of the trocar device 200. The fluid flow passageway 208 defined by the end adaptor 206 is placed in fluid flow communication with a fluid flow passageway 203 formed in the body 201 of the trocar device 200, and a trocar tip 205 extends from the body 201 of the trocar device 200 and defines a fluid flow passageway 207, which is configured to extend into the pleural cavity of a patient. Like the chest drainage device 10 and the pressure indicator assembly 100, the trocar device 200 utilizes a boss 240 for mounting the pressure indicator 228 and for defining an inlet 258 for atmospheric air. A pin 242 is similarly provided for alignment with an alignment hole 244 of the pressure indicator 228.

It will be understood that the trocar device 200 illustrated in FIGS. 10 and 11 can be utilized by a medical professional to monitor the pressure in the pleural cavity of a patient. More specifically, the trocar device 200 both provides access to the patient's pleural cavity and detects sub-atmospheric pressure in the pleural cavity and optionally provides a measurement or indication of the sub-atmospheric pressure, either quantitatively or qualitatively. It will also be appreciated that a variety of devices can be provided with a pressure indicator according to aspects of this invention in order to confirm whether or not that device has in fact been positioned within the pleural cavity. In other words, if a medical device is configured either to extend into the pleural cavity of a patient or to avoid entrance into the pleural cavity, then such device can be configured according to aspects of this invention to confirm that it has or has not entered the pleural cavity.

Referring now to FIGS. 12 and 13, the multi-chamber system 300 illustrated in those Figures exemplifies an additional application for the pressure is indicator; namely, to qualitatively or quantitatively measure or detect a pressure differential between two chambers. The two chambers may be the chambers of a chest drainage device such as chest drainage device 10 or may be chambers of any other device. Also, although the schematic representation of the multi-chamber system 300 shows closed chambers, one or both of the chambers can be in fluid flow communication with other pressure-containing chambers, whether those chambers are defined by mechanical components or assemblies or by cavities of a patient or some combination thereof. Finally, although only two chambers are illustrated in the schematic representation of the multi-chamber system 300 shown in FIGS. 12 and 13, it will be appreciated that the system optionally includes at least two chambers and can include three or more chambers as well.

Like the chest drainage device 10, the pressure indicator assembly 100, and the trocar device 200, the multi-chamber device 300 utilizes a boss 340 for mounting a pressure indicator 328 and for defining an inlet 358 for atmospheric air. A pin 342 is similarly provided for alignment with an alignment hole 344 of the pressure indicator 328. The pressure indicator 328 includes a bladder, and a window 334 is provided to visualize the pressure indicator 328.

Although the invention is illustrated and described herein with reference to specific embodiments, the invention is not intended to be limited to the details shown. Rather, various modifications may be made in the details within the scope and range of equivalents of the claims and without departing from the invention.

For example, the attachment mechanism, shape, size, materials, or configuration of the bladder of the pressure indicator are optionally modified in order to vary the performance of the indicator. Such modification can be made to configure the indicator for operation within a different, broader, or narrower range of pressures.

Also, although an apparatus such as a sub-atmospheric pressure indicator 28 has been disclosed for indicating the presence of sub-atmospheric pressure within a collection chamber 18 of a device such as a chest drainage device, the sub-atmospheric pressure indicator 28 including a bladder 48 configured to be positioned within the collection chamber 18 and coupled for fluid flow communication with atmosphere, the pressure indicator can alternatively be configured to indicate positive pressure.

That is, the pressure indicator could be positioned in a chamber in fluid flow communication with atmosphere and bladder 48 could be configured for fluid flow communication with a chamber. In this alternative configuration, supra-atmospheric pressures generated within the chamber would result in inflation of bladder 48 causing concavity 52 formed therein to contract in response to the supra-atmospheric pressure in the chamber. Surfaces 66 and 68 associated with bladder 48 are configured to move toward one another upon contraction of the concavity 52 of the bladder 48, for example, thereby indicating supra-atmospheric pressure within the chamber. Accordingly, a pressure indicator according to aspects of this invention can be configured for use in a wide variety of positive or negative pressure applications and is not limited to the use of sub-atmospheric pressure or suction.

Other modifications can be made within the scope of the invention, which is defined in the appended claims.

What is claimed:

1. An apparatus for indicating intra-pleural pressure, said apparatus comprising:
   a chamber having an interior region configured to be coupled for fluid flow communication with the pleural cavity of a patient such that the pressure in the interior region of the chamber corresponds substantially to the pressure in the pleural cavity of the patient;
   a bladder positioned within the interior region of said chamber, said bladder having an interior in fluid flow communication with atmosphere such that the pressure in the interior of the bladder corresponds substantially to atmospheric pressure, said bladder also having a concavity formed therein and configured to contract or expand in response to pressure in the pleural cavity; and
   surfaces associated with said bladder are configured to move with respect to one another upon contraction or expansion of said concavity of said bladder, thereby indicating intra-pleural pressure in the pleural cavity of the patient.

2. The chest drainage device according to claim 1, further comprising a cover, said bladder being coupled to said cover.

3. The chest drainage device according to claim 2, further comprising a pressure scale applied to said cover, at least one of said surfaces associated with said bladder being movable with respect to said pressure scale to indicate a pressure on said pressure scale.

4. The chest drainage device according to claim 2, said cover defining an inlet for atmosphere and said bladder being coupled for fluid flow communication with said inlet.

5. The apparatus according to claim 1, wherein said surfaces associated with said bladder are configured to move toward one another upon contraction of said concavity of said bladder.

6. The apparatus according to claim 1, said bladder being coupled for fluid flow communication to atmosphere, and said bladder having a concavity formed therein and configured to contract or expand in response to sub-atmospheric pressure in the pleural cavity of the patient.

7. The apparatus according to claim 1, said apparatus being configured to qualitatively indicate intra-pleural pressure in the pleural cavity of the patient.

8. The apparatus according to claim 1, said apparatus being configured to quantitatively indicate intra-pleural pressure in the pleural cavity of the patient.

9. The apparatus according to claim 1, at least one of said surfaces comprising an edge portion of said apparatus.

* * * * *